(12) United States Patent
Pullagurla et al.

(10) Patent No.: US 10,077,251 B2
(45) Date of Patent: Sep. 18, 2018

(54) PROCESS FOR THE SYNTHESIS OF DABIGATRAN ETEXILATE AND ITS INTERMEDIATES

(71) Applicant: Biophore India Pharmaceuticals PVT. Ltd., Hyderabad (IN)

(72) Inventors: Manik Reddy Pullagurla, Hyderabad (IN); Jagadeesh Babu Rangisetty, Hyderabad (IN); Mecheril Valsan Nandakumar, Hyderabad (IN)

(73) Assignee: Biophore India Pharmaceuticals PVT. Ltd., Balanagar, Hyderabad (IN)

( * ) Notice: Subject to any disclaimer, the term of this patent is extended or adjusted under 35 U.S.C. 154(b) by 0 days.

(21) Appl. No.: 15/291,087

(22) Filed: Oct. 12, 2016

(65) Prior Publication Data

US 2017/0050948 A1  Feb. 23, 2017

Related U.S. Application Data

(62) Division of application No. 14/438,995, filed as application No. PCT/IN2013/000652 on Oct. 28, 2013, now Pat. No. 9,533,971.

(30) Foreign Application Priority Data

Oct. 29, 2012  (IN) .......................... 4484/CHE/2012

(51) Int. Cl.
    *C07D 401/12* (2006.01)
    *C07D 213/75* (2006.01)
(52) U.S. Cl.
    CPC ......... *C07D 401/12* (2013.01); *C07D 213/75* (2013.01)
(58) Field of Classification Search
    CPC . C07D 213/75; C07D 401/12; C07D 1401/12
    USPC .............................. 546/273.4, 309
    See application file for complete search history.

(56) References Cited

U.S. PATENT DOCUMENTS 9,533,971 B2 *  1/2017  Pullagurla ............ C07D 213/75
2003/0004356 A1  1/2003  Ries et al.

FOREIGN PATENT DOCUMENTS

| DE | 19962329 A | 6/2001 |
| WO | WO9837075 A | 8/1998 |
| WO | WO200001704 A3 | 1/2000 |
| WO | WO2006000353 A | 1/2006 |
| WO | WO2007071742 A1 | 6/2007 |
| WO | WO2007071743 A1 | 6/2007 |
| WO | WO2008095928 A1 | 8/2008 |
| WO | WO2009111997 A1 | 9/2009 |
| WO | WO2009153214 A1 | 12/2009 |
| WO | WO2012004397 A1 | 1/2012 |
| WO | WO2013111163 A2 | 8/2013 |

\* cited by examiner

*Primary Examiner* — Patricia L Morris
(74) *Attorney, Agent, or Firm* — Ling Wu; Stephen Yang; Ling and Yang Intellectual Property

(57) ABSTRACT

The present invention describes an improved process for the preparation of Dabigatran Etexilate (Formula-VII) or it's pharmaceutically acceptable salt for the treatment of thrombosis, cardiovascular diseases etc. and intermediates involved in the synthesis.

Formula VII

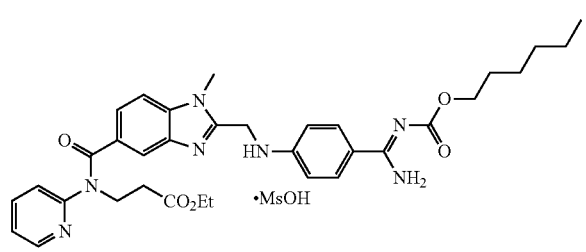

7 Claims, No Drawings

PROCESS FOR THE SYNTHESIS OF DABIGATRAN ETEXILATE AND ITS INTERMEDIATES

RELATED APPLICATION

This is a divisional application of application Ser. No. 14/438,995, filed Apr. 28, 2015, which is a nation stage application under 35 U.S.C. 154(d)(4) and 35 U.S.C. 371 for PCT/IN2013/000652, filed Oct. 28, 2013.

FIELD OF INVENTION

The present invention describes an improved process for the preparation of Dabigatran Etexilate (VII), a pharmaceutically acceptable salt for the treatment of thrombosis, cardiovascular diseases etc., and its intermediates involved in the synthesis.

BACKGROUND OF THE INVENTION

Dabigatran Etexilate Mesylate (VII), chemically known as β-Alanine, N-[[2-[[[4-[[[(hexyloxy) carbonyl] amino] iminomethyl] phenyl]amino]methyl]-1-methyl-1H-benzimidazol-5-yl]carbonyl]-N-2-pyridinyl-,ethyl ester, methanesulfonate, is a thrombin inhibitor. The structure of Dabigatran Etexilate in the form of mesylate salt is as shown below in compound of formula (VII):

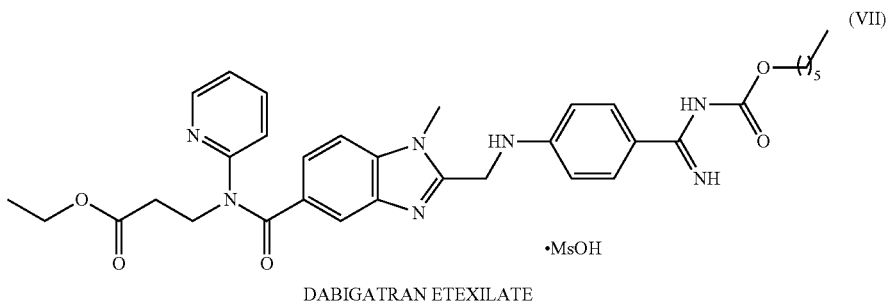

DABIGATRAN ETEXILATE

The compound of formula VII above also represents Dabigatran Etexilate (Wherein MsOH is absent in formula VII).

Dabigatran etexilate was first described in International patent application WO 98/37075 and the process for manufacture was reported in WO 2006/000353 and also in J. Med. Chem, 2002, 45, 1757 by N. Hauel et al.

Two general routes have been reported for the synthesis of Dabigatran etexilate (VII). The first process was disclosed in WO98/37075 and a modification of the first route has been described in WO 2006/000353. Both the synthetic routes start from the 3-nitro-4-methylamino-benzoic acid and are presented in Scheme 1.

Scheme 1

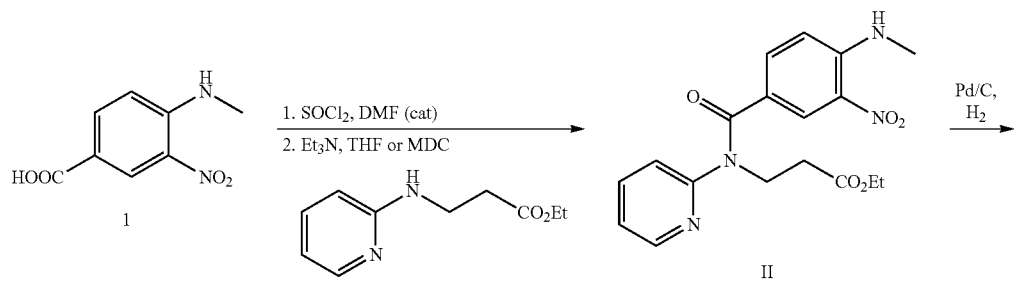

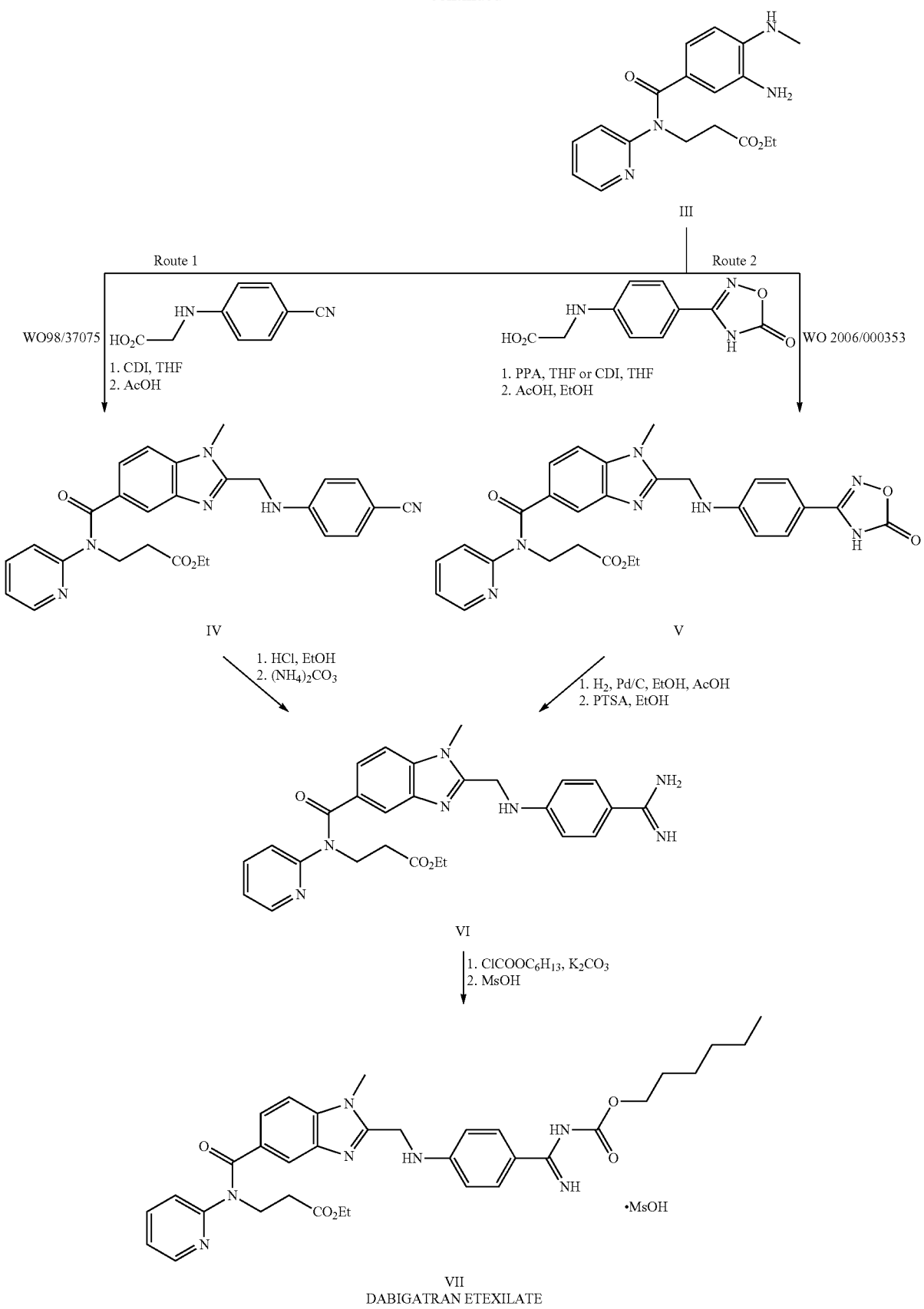
VII
DABIGATRAN ETEXILATE

Both the routes (Scheme-1) involved three common intermediates II, III and VI, of which VI can be obtained from either IV or V depending on the substituted glycine used for the synthesis. According to the previous reports, all the intermediates required column purification to prepare substantially pure Dabigatran Etexilate and the processes are not suitable for industrial scale production of the same. The synthesis of intermediate II has been reported in several patents and require either a chromatographic purification or a tedious purification procedure such as converting into the HCl salt followed by recrystallization to obtain 97% pure intermediate II. In both cases, the yield is less than 50%. Similarly, Intermediate III is one of the key intermediates in the Dabigatran Etexilate synthesis and the process involves the reduction of nitro group either by hydrogenation in presence of Pd/C or in presence of sodium dithionite. Both the methods (Scheme-1, catalyst Pd/C) resulted in the formation of product with higher level of impurities. WO 2012/004397 reports the product as a solid and in US 20110082299 (WO 2009/111997) wherein the reduction of nitro group is performed in presence of Sodium dithionite, the intermediate is reported as a dark red coloured viscous liquid and used without further purification. However, it is essential that the key intermediate IHI must be very pure to obtain the intermediate VI as very pure compound thereby isolating the Dabigatran Etexilate API with required purity in the final stage.

Similarly, the intermediates IV and V prepared by either CDI or PPA mediated coupling with glycine derivatives followed by acetic acid mediated cyclization resulted in the formation of highly impure products, and purified by either column chromatography or by converting the crude reaction mixture to suitable salts. Both the methods afforded low yield and purity thereby the process is not suitable for the commercial scale production of Dabigatran Etexilate.

OBJECT OF THE INVENTION

The primary object of the invention is to develop an improved process for the industrial scale production of Dabigatran Etexilate (VII) or its pharmaceutically acceptable salt such as mesylate salt.

Another object of the invention is to provide a suitable purification method for preparation of intermediate II.

Another aspect of the invention is to provide an improved process for preparation of compound of formula III.

Further object of the invention is to provide an efficient process for preparation of compound of formula IV.

DETAILED DESCRIPTION OF THE INVENTION

Most of the prior art processes for the synthesis of Dabigatran Etexilate require tedious purification methods for the intermediates II, III, IV, V and VI. In earlier reports, the intermediate II was purified either by preparing the HCl or HBr salt or by column chromatography, which resulted in low yield and purity of II.

One aspect of the invention is to obtain a suitable method for purifying the intermediate II in the free base form. The known art for the purification of intermediate II is by converting it in to the corresponding acid salts and recrystallization of the salt, which in turn would result in the yield loss.

Inventors have found a novel method of purifying the free base of intermediate II by recrystallizing the compound in an aprotic solvent such as hexane, toluene, xylene or the like. Preferably the solvent used is hexane or a mixture of toluene and hexane.

The temperature used for the recrystallization is from 50-100° C. followed by cooling to 30-0° C.

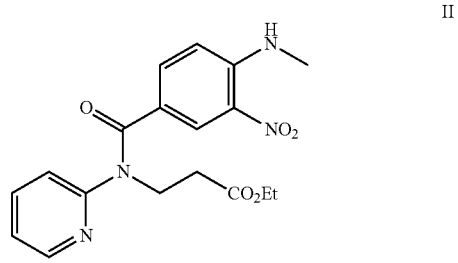 [SMILES: CCOC(=O)CCN(C(=O)c1ccc(NC)c([N+](=O)[O-])c1)c1ccccn1]

The reduction of intermediate II to the corresponding amino compound (III) is reported using hydrogenation in presence of Pd/C or with sodium dithionite. Both the methods yielded the product with higher level of impurities, which needs lengthy purification methods. The main drawback with the reported sodium dithionite reduction in WO 2009111997 is the formation of impurities. The intermediate III is isolated as brown viscous oil and proceeded to the next stage without further purification. The inventors have found that such process without purification results in low yields and low purity of the Formula IV, the key intermediate in the Dabigatran Etexilate synthesis.

Another aspect of the invention is to develop an economical and scalable process for the preparation of III without affecting the yield and purity. Inventors have found that the combination of sodium dithionite with an organic or inorganic base as reducing agent dramatically simplified the reduction process and yielded intermediate III with excellent yield and purity as a solid.

The inorganic base used is selected from $Na_2CO_3$, $K_2CO_3$, $NaHCO_3$ and the like or an organic base is selected from triethyl amine, pyridine and DIPEA (N,N-Diisopropylethylamine); preferably the base used is inorganic base, more preferably the inorganic base is potassium carbonate ($K_2CO_3$).

The reduction is carried out in presence of a base in a water miscible solvent such as tetrahydrofuran, alcohols, acetone, or ether solvents in combination with water preferably in a mixture of dioxane and water. The product is purified by recrystallization using ethyl acetate as solvent.

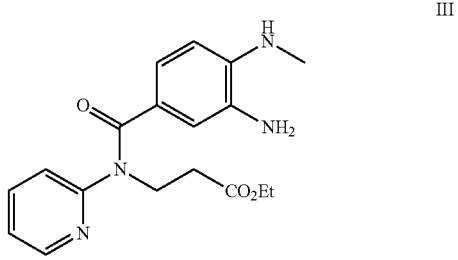 [SMILES: CCOC(=O)CCN(C(=O)c1ccc(NC)c(N)c1)c1ccccn1]

Since intermediate IV is a key intermediate in the synthesis of Dabigatran Etexilate, substantially pure IV is necessary to achieve good conversion and purity in the next stages of the process. In the prior art the synthesis has been achieved by the CDI mediated amide formation in THF at 66-70° C. for 5 h, followed by the acetic acid mediated cyclization. The reaction produces a highly impure intermediate IV and it required tedious procedure for the purification such as column chromatography or converting it into the corresponding acid salts. In US 20110224441, the intermediate IV was purified by making the oxalate salt, in WO 2008095928 as the HBr salt and in WO 98/37075 the same was purified by column chromatography.

Another object of the invention provides an improved process for the conversion of intermediate III to IV using DCC or EDC optionally in the presence of HOBt (hydroxybenzotriazole) at 25-35° C. followed by acetic acid mediated cyclization to the corresponding benzimadazole intermediate IV. The advantage of the new methodology compared with the reported CDI mediated coupling reaction is the milder reaction conditions and low level of impurity formation during the process.

The reaction may also be carried using DCC (dicyclohexylcarbodiimide) or EDC (1-Ethyl-3-(3-dimethylaminopropyl)carbodiimide) in presence of an activating agent such as HOBt, N-hydroxy succinimide, DMAP (4-dimethylaminopyridine) or the like in aprotic solvent at temperatures ranging from 20-40° C.

The present invention also provides a method for purifying the intermediate IV in the free base form by recrystallization using a suitable solvent. The solvent used for the recrystallization is selected from ethyl acetate, isobutyl acetate, isopropyl acetate, IPA at temperatures ranging from 0-25° C. and preferably ethyl acetate or IPA.

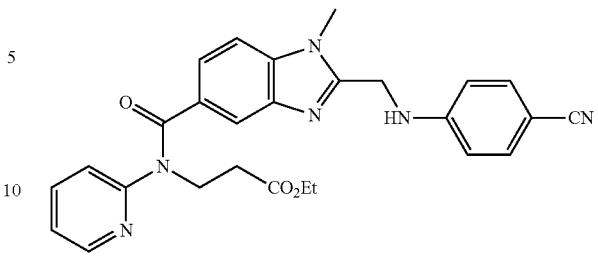

Intermediate VI is prepared by the reaction of IV with HCl and ethanol followed by reaction with ammonium carbonate using a known art for converting cyano to the corresponding amidines.

Dabigatran Etexilate synthesis is completed by the reaction of intermediate VI with n-hexyl chloroformate in presence of a suitable base in a protic solvent or water or mixture of water and an organic solvent.

Finally the Dabigatran Etexilate free base is converted in to the mesylate salt by reacting with methanesulphonic acid in acetone.

The present invention is schematically represented as follows in Scheme-2.

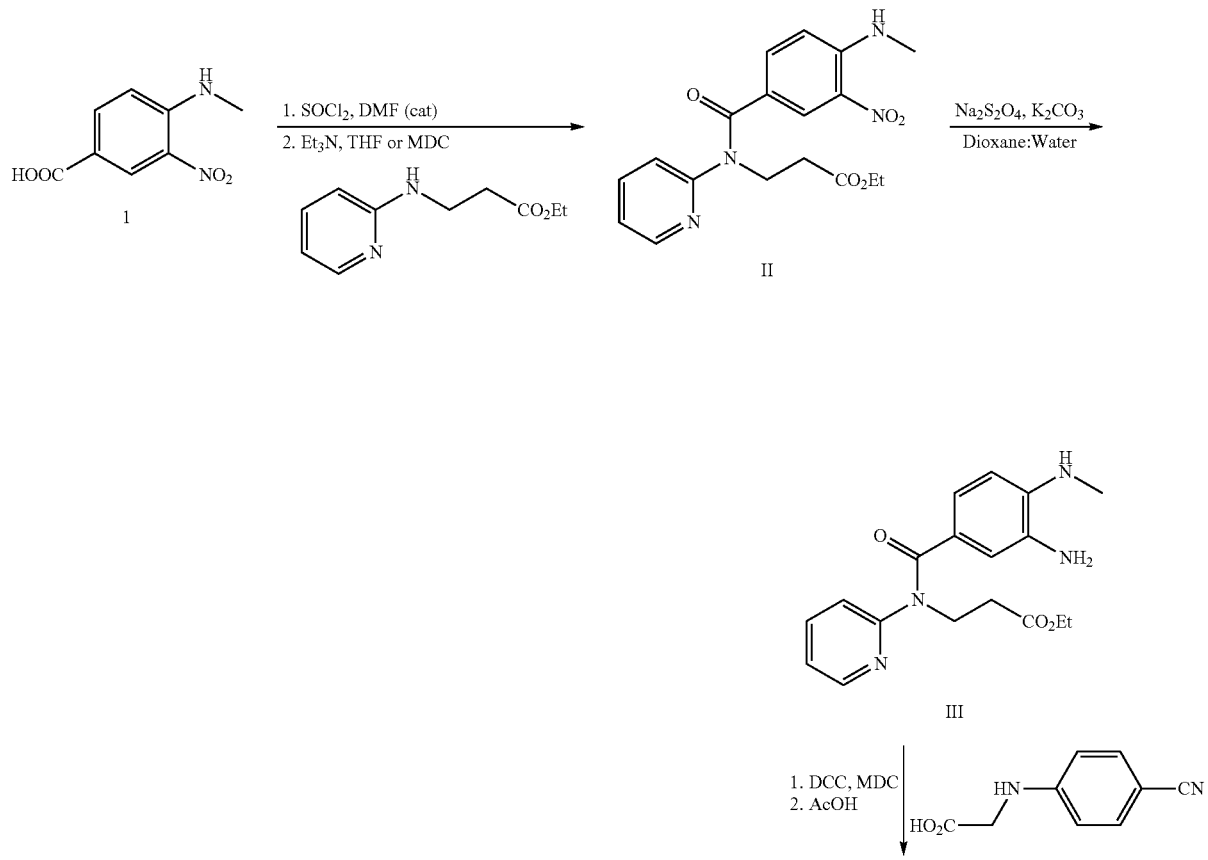

Scheme-2

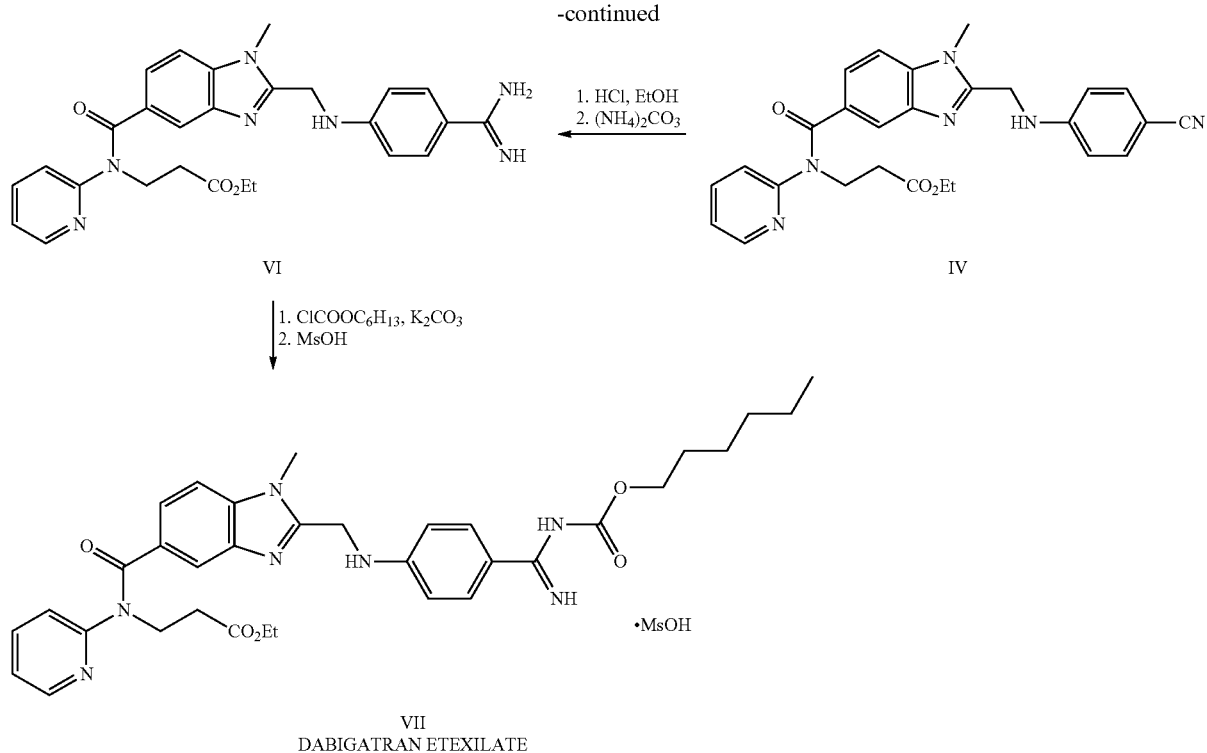

VI → IV (1. HCl, EtOH; 2. (NH4)2CO3)

1. ClCOOC6H13, K2CO3
2. MsOH

VII
DABIGATRAN ETEXILATE
·MsOH

In conclusion, the authors have disclosed an improved industrial scale process for the synthesis of Dabigatran Etexilate or its mesylate salt form (VII) and it intermediates.

EXAMPLE 1

Preparation of ethyl 3-[[4-(methylamino)-3-nitrobenzoyl](pyridin-2-yl)amino]-propanoate (II)

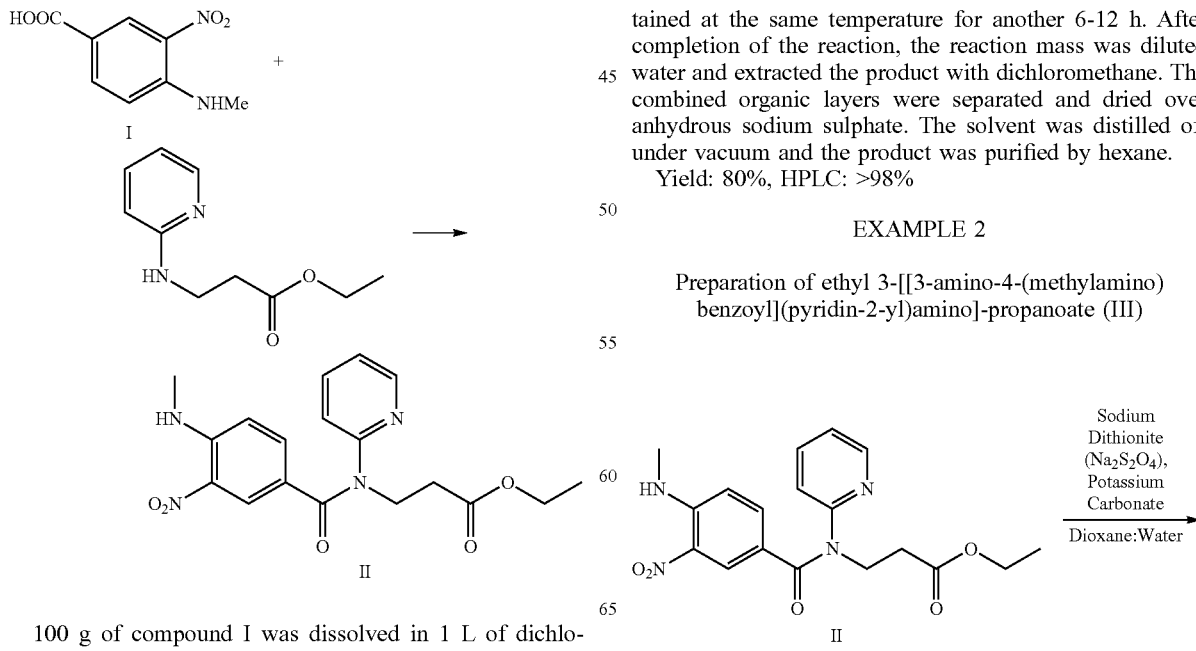

100 g of compound I was dissolved in 1 L of dichloromethane under nitrogen atmosphere and cooled to 0-5° C. Thionyl chloride was added to the reaction mixture for 1 h and the reaction mixture was boiled to reflux. The reaction mass is maintained under the same temperature for 5-6 h. After completion of the reaction, excess thionyl chloride was removed by co-distillation with dichloromethane and finally the solvent was completely removed under vacuum. The acid chloride was then dissolved in dichloromethane under an inert atmosphere and triethyl amine was added to the reaction mixture. To the reaction mixture was added slowly a solution of ethyl-3-(pyridine-2-ylamino) propanoate in dichloromethane. The reaction mixture was maintained at the same temperature for another 6-12 h. After completion of the reaction, the reaction mass was diluted water and extracted the product with dichloromethane. The combined organic layers were separated and dried over anhydrous sodium sulphate. The solvent was distilled off under vacuum and the product was purified by hexane.

Yield: 80%, HPLC: >98%

EXAMPLE 2

Preparation of ethyl 3-[[3-amino-4-(methylamino) benzoyl](pyridin-2-yl)amino]-propanoate (III)

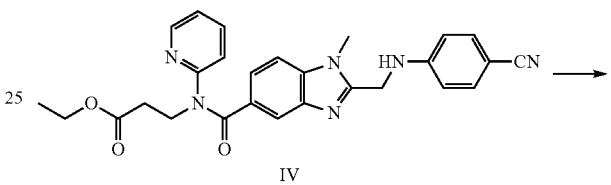

III 100 g of compound II was dissolved in 1 L of a mixture of dioxane and water and heated the reaction mixture to 50° C. Sodium dithionite (4.5 equiv.) and potassium carbonate (0.3 equiv.) was added to the reaction mixture and maintained at the same temperature for 2-6 h. After completion of the reaction, filtered the reaction mixture and evaporated the solvent. Water was added to the crude mixture and extracted the product with ethyl acetate. The organic layer was dried over anhydrous sodium sulphate and filtered. The solvent was removed under vacuum yielded the compound III as a brown viscous liquid. The product was purified by recrystallization from ethyl acetate.

Yield: 80%; HPLC: >98%

EXAMPLE-3

Preparation of 3-([2-[(4-cyanophenyl amino)-methyl]-1-methyl-1H-benzimidazole-5-carbonyl]-pyridin-2-yl-amino)ethyl propionate(IV)

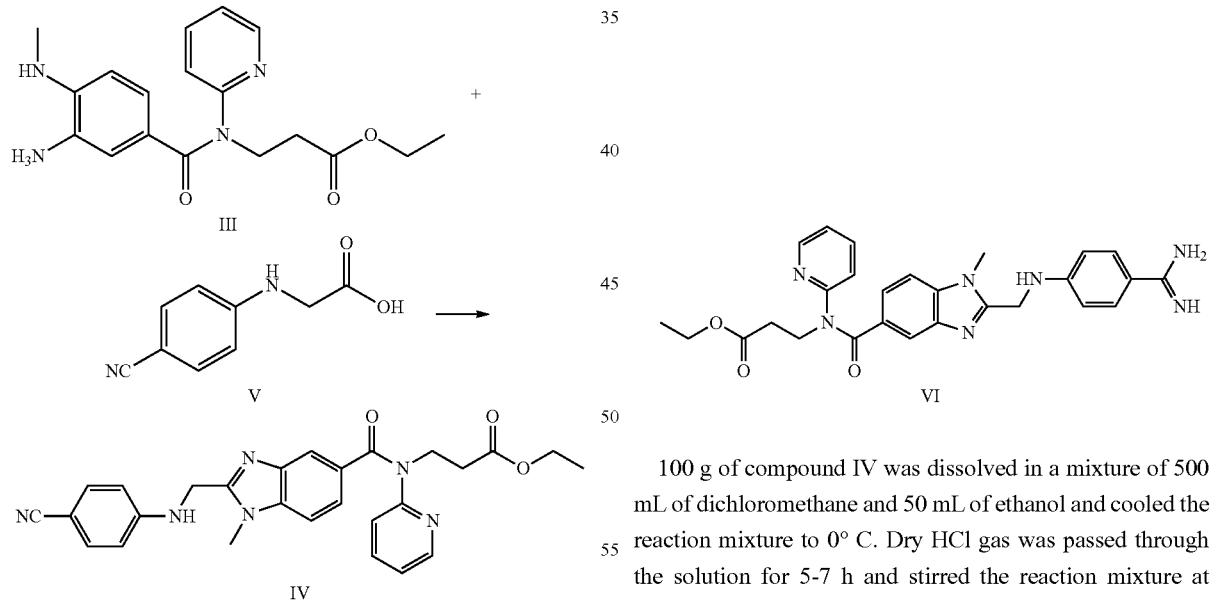

100 g of compound III was dissolved in dichloromethane under nitrogen atmosphere. Added 41 mL of triethyl amine and 39 g of HOBt to the reaction mass and stirred for 15 minutes. Cooled to 20° C. and added 77 g of N-(4-Cyanophenyl) glycine (formula V) and a solution of DCC in dichloromethane to the reaction mass and stirred for 30 minutes. Filtered the precipitated solids, dried the filtrate with anhydrous sodium sulphate and removed solvent under vacuum. Acetic acid was added to the crude mass and refluxed for 2-6 h. After completion of the reaction, cooled the reaction mixture to room temperature and water was added. The pH of the solution was adjusted to 6-8 and extracted the product with dichloromethane. The organic layer was collected, dried over sodium sulphate and removed under vacuum. The crude material obtained was purified by recrystallization in ethyl acetate.

Yield: 84%, HPLC: >97%

EXAMPLE-4

Preparation of N-[([(amidinophenyl)-amino]methyl)-1-methyl-1H-benzimidazole-5-carbonyl]-N-(2-pyridyl)-3-aminopropionic acid (VI)

100 g of compound IV was dissolved in a mixture of 500 mL of dichloromethane and 50 mL of ethanol and cooled the reaction mixture to 0° C. Dry HCl gas was passed through the solution for 5-7 h and stirred the reaction mixture at room temperature for another 36 h. After completion of the reaction, ethanol was removed from the reaction mixture and 200 g of ammonium carbonate and 500 mL of ethanol was added. Stirred the reaction mass for another 24 h. Filtered the solids and the solvent was removed under vacuum. The product was purified by recrystallization using a mixture ethyl acetate and ethanol.

Yield: 90%, HPLC: >98%

EXAMPLE-5

Preparation of Ethyl N—[(N'-hexyloxycarbonyl)amidino]phenyl)amino]methyl)-1-methyl-1H-benzimidazole-5-carbonyl]-N-(2-pyridyl)-3-aminopropionate Mesylate (VII)

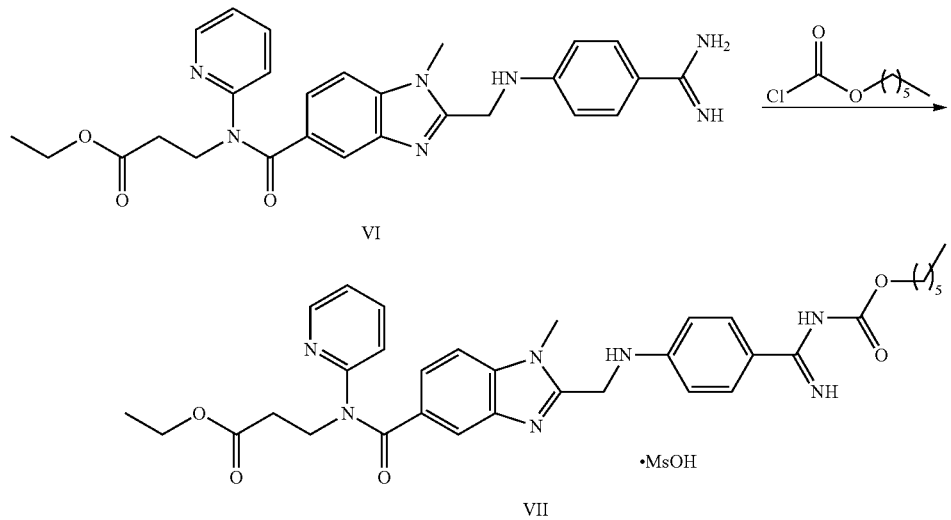

Method: A 50 g of compound VI was dissolved in 400 ml of acetone and 250 ml of Water, Cool reaction mixture to 10-15° C. 30 g of Potassium carbonate added lot wise and 3.25 ml of n-hexyl chloroformate was added slowly to the reaction mixture and stirred for another 1 h. After completion of the reaction the precipitated product is filtered off washed with acetone/Water and material was recrystallized by using acetone and Water. Product is dissolved in 250 ml of acetone and cooled to 10-15° C. 7 g of methane sulphonic acid in acetone was slowly added to the reaction mixture with stirring and the precipitated material was isolated by filtration. The product was purified by recrystallizating from acetone. Yield: 60 g (80-85%) HPLC purity 99.5%.

Method B:

100 g of compound VI was dissolved in 500 mL of dry dichloromethane and cooled the reaction mixture to 0-5° C. 100 mL of triethyl amine was slowly added to the reaction mixture and stirred for 15 minutes. Added 65 mL of n-hexyl chloroformate to the reaction mixture for a period of 15 minutes and the stirring was continued for another 1 h. After completion of the reaction, water was added to the reaction mixture and extracted the product with dichloromethane. The organic layer was dried over anhydrous sodium sulphate and removed the solvent under vacuum. The crude reaction mixture was purified by recrystallization using ethyl acetate. The product thus obtained was dissolved in 500 mL of acetone and cooled the solution to 0-5° C. 10 mL of Methane sulphonic acid was slowly added to the reaction mixture. The precipitated solid was isolated and purified by recrystallization using acetone.

Yield: 75%, HPLC: ≥99.5%

Abbreviations

Where ever short form (abbreviation) is used/mentioned in the specification, it defines following corresponding full name, unless otherwise it is mentioned specifically.

| | |
|---|---|
| DIPEA | N,N-Diisopropylethylamine |
| DMAP | 4-dimethylaminopyridine |
| DCC | dicyclohexylcarbodiimide |
| EDC | 1-Ethyl-3-(3-dimethylaminopropyl)carbodiimide |
| IPA | Isopropyl Alcohol |
| HCl | Hydrochloric Acid |

-continued

| | |
|---|---|
| HBr | Hydrobromic Acid |
| CDI | 1,1'-Carbonyldiimidazole |
| PPA | Polyphosphoric acid |
| HOBt | Hydroxybenzotriazole |
| THF | Tetrahydrofuran |
| Na$_2$CO$_3$, | Sodium Carbonate |
| K$_2$CO$_3$, | Potassium Carbonate |
| NaHCO$_3$ | Sodium Bicarbonate |

What we claim is:

1. A process for preparation of Dabigatran Etexilate or its mesylate salt of formula VII (VII)

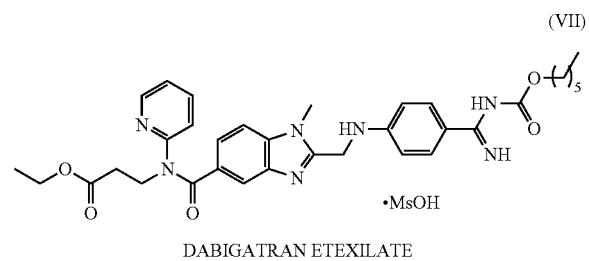

DABIGATRAN ETEXILATE comprising the steps of:
i) reduction of a nitro compound of formula II to amine compound of formula III,

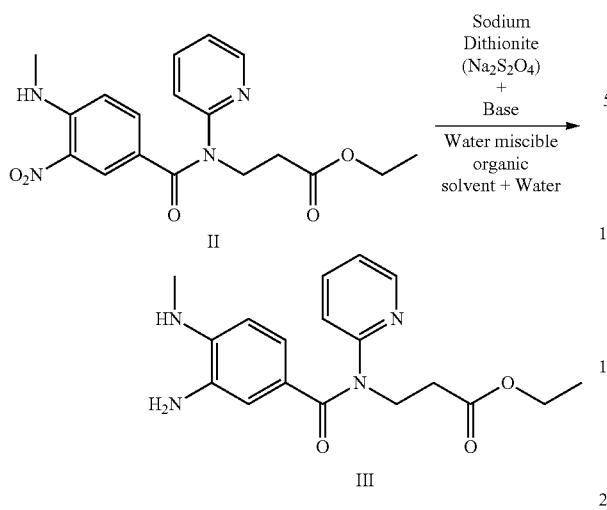

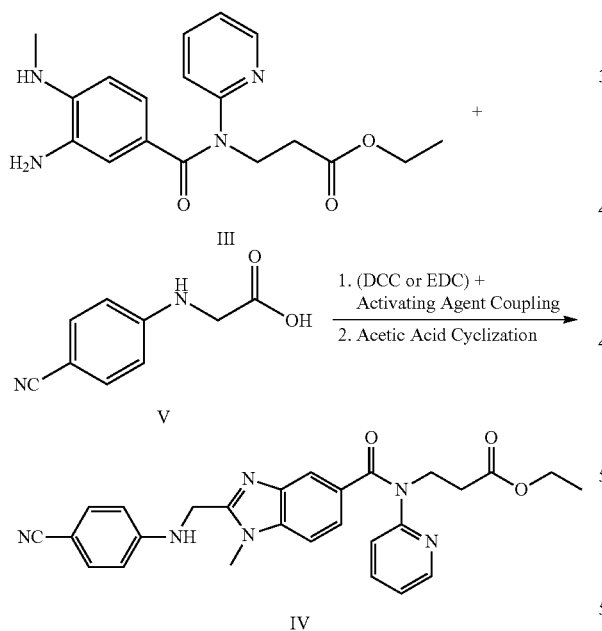

wherein the said reduction is performed in the presence of a combination of sodium dithionite and a base as reducing agent, and
wherein the said reduction is performed in presence of a water miscible organic solvent in combination with water;

ii) coupling reaction of compound of formula III and N-(4-cyanophenyl)glycine of formula V to produce a compound of formula IV, wherein the coupling takes place with dicyclohexylcarbodiimide (DCC) or 1-Ethyl-3-(3-dimethylaminopropyl)carbodiimide (EDC) in presence of an activating agent at a temperature range of 25-35° C., followed by acetic acid mediated cyclization to give compound of formula IV;

iii) treating the compound of formula IV with HCl in ethanol at 0° C., followed by treating the residue with ammonium carbonate to produce a compound of formula VI

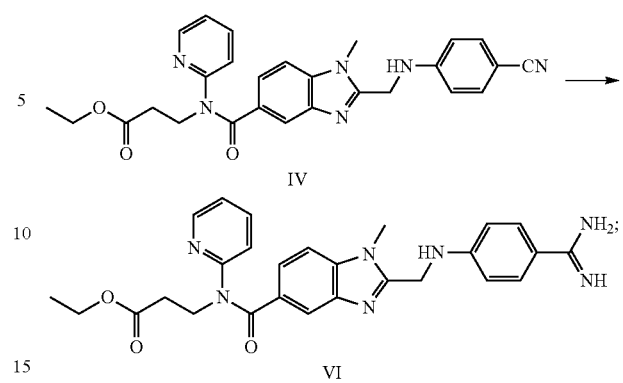

iv) treating the compound of formula VI with n-hexyl chloroformate in the presence of a base to obtain Dabigatran Etexilate of formula VII; optionally converting Dabigatran Etexilate to mesylate salt by treating it with methane sulphonic acid in acetone

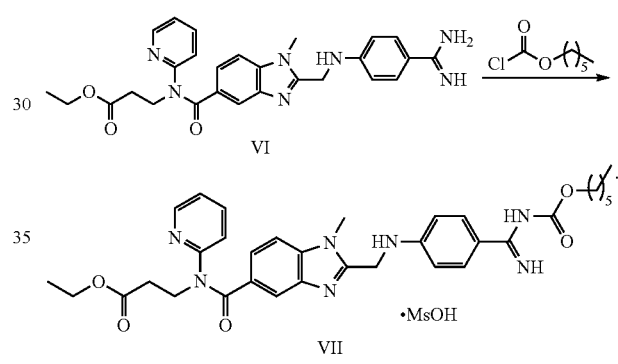

2. The process as claimed in claim 1, wherein the base is inorganic base selected from the group consisting of sodium carbonate, potassium carbonate and sodium bicarbonate.

3. The process as claimed in claim 1, wherein the base is organic base selected from the group consisting of triethylamine, pyridine and N,N-Diisopropylethylamine (DIPEA).

4. The process as claimed in claim 1, wherein the reduction reaction is performed in presence of a combination of sodium dithionite and potassium carbonate as reducing agent, and a combination of dioxane and water as solvent.

5. The process as claimed in claim 1, wherein the activating agent in step ii) is selected from the group consisting of hydroxybenzotriazole (HOBt), 4-dimethylaminopyridine (DMAP) and N-hydroxysuccinimide.

6. The process as claimed in claim 1, wherein the compound of formula IV is obtained in the free base form by recrystallization using a solvent selected from ethyl acetate, isobutyl acetate, isopropyl acetate or Isopropyl alcohol at temperature ranging from 0-25° C.

7. The process as claimed in claim 1, wherein the compound of formula II is prepared by coupling the compound of formula I with ethyl-3-(pyridine-2-ylamino) propanoate, via the intermittent acid chloride formation

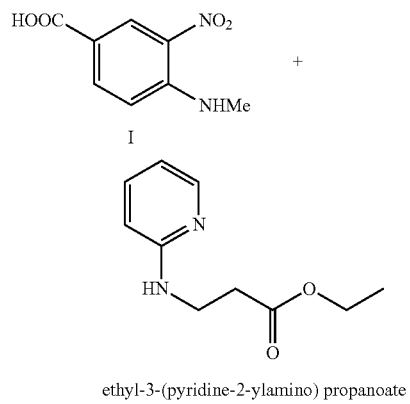

ethyl-3-(pyridine-2-ylamino) propanoate

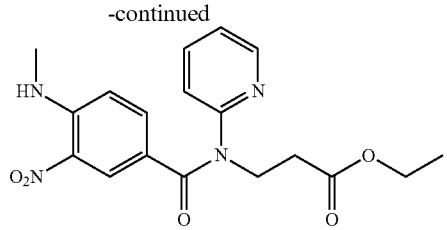

II

Recrystallization | Aprotic solvent 50-100° C. followed by cooling to 30-0° C.

Free base of Formula II wherein the compound of formula II as formed is purified in free base form by recrystallizing the compound II in an aprotic solvent selected from hexane, toluene and xylene or mixture of toluene and hexane at temperature range of 50-100° C. followed by cooling to 30-0° C.

* * * * *